United States Patent [19]

Van Der Puy et al.

[11] Patent Number: 5,696,307

[45] Date of Patent: Dec. 9, 1997

[54] HYDROFLUOROALKANES AS CLEANING AND DEGREASING SOLVENTS

[75] Inventors: Michael Van Der Puy, Cheektowaga; Rajat Subhra Basu, East Amherst; David Nalewajek, West Seneca; Lois A. Ellis, Orchard Park, all of N.Y.

[73] Assignee: AlliedSignal Inc., Morris Township, N.J.

[21] Appl. No.: 184,810

[22] Filed: Jan. 21, 1994

[51] Int. Cl.⁶ .................. C07C 19/08; C07C 23/06
[52] U.S. Cl. .................. 570/134; 134/40; 252/364; 570/132
[58] Field of Search ........................... 570/134

[56] References Cited

U.S. PATENT DOCUMENTS

| | | | |
|---|---|---|---|
| 2,980,740 | 4/1961 | Hasek et al. | 570/134 |
| 4,157,979 | 6/1979 | Walters | 570/134 |
| 4,541,943 | 9/1985 | Powell | 570/134 |
| 4,559,154 | 12/1985 | Powell | 570/134 |
| 5,064,559 | 11/1991 | Merchant et al. . | |
| 5,064,560 | 11/1991 | Merchant . | |
| 5,073,288 | 12/1991 | Anton . | |
| 5,073,290 | 12/1991 | Anton et al. . | |
| 5,073,291 | 12/1991 | Robeck et al. | 252/171 |
| 5,076,956 | 12/1991 | Anton . | |
| 5,084,199 | 1/1992 | Anton . | |
| 5,100,572 | 3/1992 | Merchant | 570/134 |
| 5,182,042 | 1/1993 | Van Der Puy | 252/172 |
| 5,194,170 | 3/1993 | Merchant et al. | 252/67 |
| 5,196,137 | 3/1993 | Merchant | 252/172 |
| 5,219,488 | 6/1993 | Basu et al. | 252/171 |
| 5,219,489 | 6/1993 | Swan et al. | 252/171 |
| 5,219,490 | 6/1993 | Basu et al. . | |
| 5,221,493 | 6/1993 | Merchant et al. . | |
| 5,225,099 | 7/1993 | Basu et al. . | |
| 5,250,208 | 10/1993 | Merchant et al. | 252/67 |
| 5,250,213 | 10/1993 | Rozen et al. | 252/162 |
| 5,259,983 | 11/1993 | Van Der Puy et al. | 252/171 |
| 5,266,231 | 11/1993 | Robeck et al. | 252/171 |
| 5,266,232 | 11/1993 | Robeck et al. | 252/171 |
| 5,268,120 | 12/1993 | Michaud | 252/162 |
| 5,268,121 | 12/1993 | Michaud | 252/171 |
| 5,268,122 | 12/1993 | Rao et al. | 570/134 |
| 5,274,189 | 12/1993 | Napps et al. | 570/134 |
| 5,274,190 | 12/1993 | Nappa et al. | 570/142 |
| 5,275,669 | 1/1994 | Van Der Puy et al. . | |
| 5,288,422 | 2/1994 | Basu et al. . | |
| 5,290,473 | 3/1994 | Basu et al. . | |
| 5,348,681 | 9/1994 | Desbiendras et al. | 252/172 |
| 5,350,534 | 9/1994 | Michaud | 252/171 |
| 5,352,375 | 10/1994 | Swan et al. | 252/171 |
| 5,531,916 | 7/1996 | Merchant | 510/412 |

FOREIGN PATENT DOCUMENTS

| | | |
|---|---|---|
| 0 381 986 | 1/1990 | European Pat. Off. . |
| 0 431 458 A1 | 11/1990 | European Pat. Off. . |
| 0 516 029 A1 | 2/1992 | European Pat. Off. . |
| 0 519 432 A2 | 6/1992 | European Pat. Off. . |
| Sho 54-34485 | 3/1979 | Japan . |
| Sho 54-87711 | 7/1979 | Japan . |
| Sho 54-131099 | 10/1980 | Japan . |
| 5-302098 | 11/1993 | Japan . |
| Hei 6-15105 | 1/1994 | Japan . |
| Hei 6-17096 | 1/1994 | Japan . |
| Hei 6-41588 | 2/1994 | Japan . |
| Hei 6-41589 | 2/1994 | Japan . |
| Hei 6-41590 | 2/1994 | Japan . |
| Hei 6-49490 | 2/1994 | Japan . |
| Hei 6-49491 | 2/1994 | Japan . |
| Hei 6-49492 | 2/1994 | Japan . |
| Hei 6-205903 | 7/1994 | Japan . |
| WO 92/06941 | 4/1992 | WIPO . |
| WO 92/19706 | 12/1992 | WIPO . |
| WO 93/05002 | 3/1993 | WIPO . |
| WO 93/08240 | 4/1993 | WIPO . |
| WO 2/11280 | 6/1993 | WIPO . |
| WO 93/16973 | 9/1993 | WIPO . |

OTHER PUBLICATIONS

Rahman et al, J.Am.Chem.Soc., 1986, 108, 6296–6299.
Weigert, J. Org. Chem., 45, 3476–3483, 1980.
Kitamura et al, Chem. Abstracts 120:301689, 1994.
Burdon et al, Chem Abstracts 110:114257, 1989.
Russian Journal of Oganic Chemistry. Zh. Org. Khim. vol. 21, No. 7, pp. 1414–1420. 1985.

*Primary Examiner*—C. Warren Ivy
*Assistant Examiner*—Lyman H. Smith
*Attorney, Agent, or Firm*—Lois A. Gianneschi

[57] ABSTRACT

Hydrofluoroalkanes useful as solvents, especially for vapor degreasing and solvent cleaning, are one or many of the following formulae:

$$CHF_2-X-(CHF)_n-X-Y$$

wherein X is selected from the group consisting of CHF, $CF_2$ and $CH_2$, Y is $CH_3$, and n is 0, 1 or 2.

1 Claim, No Drawings

HYDROFLUOROALKANES AS CLEANING AND DEGREASING SOLVENTS

FIELD OF THE INVENTION

This invention relates to vapor degreasing and solvent cleaning and more particularly relates to the use of certain hydrofluoroalkanes for vapor degreasing and solvent cleaning.

BACKGROUND

Vapor degreasing and solvent cleaning with fluorocarbon-based solvents have found widespread use in industry for the degreasing and otherwise cleaning of solid surfaces, especially intricate parts and difficult-to-remove soils.

In its simplest form, vapor degreasing or solvent cleaning comprises exposing an object to be cleaned to the vapors of a boiling solvent. Vapors condensing on the object provide clean distilled solvent to wash away grease or other contamination. Final evaporation of solvent from the object leaves behind no residue as would be the case where the object is simply washed in liquid solvent.

In situations where it is difficult to remove soils such as where elevated temperatures are necessary to improve the cleaning action of the solvent, or for large volume assembly line operations where the cleaning of metal parts and assemblies must be done efficiently and quickly, the conventional operation of a vapor degreaser comprises immersing the part to be cleaned in a sump of boiling solvent which removes the bulk of the soil, thereafter immersing the part in a sump containing freshly distilled solvent at near room temperature, and finally exposing the part to solvent vapors over the boiling sump which condense on the cleaned part. In addition, the part can also be sprayed with distilled solvent before final rinsing.

Cold cleaning is another application where a number of solvents are used. In most cold cleaning applications, the soiled part is either immersed in the fluid or wiped with cloths or similar objects, soaked in solvents and allowed to air dry.

Solvents comprising fluorocarbons are, of course, well-known. In particular, trichlorotrifluoroethane (CFC-113) has attained widespread use in recent years as an effective, non-toxic and non-flammable agent useful in degreasing applications and other solvent cleaning applications. The problem with chlorofluorocarbons, known as CFCs, such as CFC-113, is that they are believed to cause environmental problems in connection with the ozone layer in the earth's atmosphere. Therefore, the art is seeking new fluorocarbon-based materials which provide the cleaning advantages of the known chlorofluorocarbons but which do not have an adverse effect on the ozone layer of the earth's atmosphere. Mathematical models substantiate that hydrofluorocarbons which do not contain chlorine will not adversely effect atmospheric chemistry because they are non-ozone depleting and would contribute negligibly to global warming when compared to CFCs such as CFC-113.

It is known from European Patent Application No. 043145881, published Jun. 12, 1991, that certain fluorinated aliphatic hydrocarbons may be used as cleaning compositions alone or in admixture with an organic solvent. The present invention provides a new class of fluorinated aliphatic hydrocarbons which do not contain chlorine and which are useful as degreasers and solvents.

The present invention provides a specific group of hydrofluoroalkanes useful as cleaning and degreasing solvents, which hydrofluoroalkanes are characterized by being non-flammable, having a boiling point in the range of 30° to 120° C. and fluorinated to the extent of 67 to 75 percent based on atomic weight. More particularly, the present invention provides a select group of solvents for cleaning and degreasing which are hydrofluoroalkanes characterized as containing from 3 to 6 carbon atoms, from 67 to 75 percent of fluorination on said carbon atoms based on atomic weight, and having a boiling point in the range of 30°–120° C. The present invention also provides methods for cleaning and/or degreasing components and substrates which comprises treating said components and/or substrates with an effective amount of a solvent comprising one or more hydrofluoroalkanes of this invention.

DESCRIPTION OF THE INVENTION

The hydrofluoroalkanes of the present invention have good solvent power, but do not contribute to ozone depletion. The compounds are also non-flammable and do not exhibit any flash point when tested by the Tag Open Cup Test Method—D-ASTM 1310-86 and Tag Closed Test Method—D-ASTM 56-82.

The present invention provides solvent compositions comprising certain straight chain hydrofluoroalkanes, i.e., aliphatic hydrocarbons which contain only hydrogen and fluorine as substituents. The hydrofluoroalkanes of the present invention may be characterized as being one or more fluorinated hydrocarbons as set forth hereinafter.

A preferred group of fluorinated hydrocarbons of this invention are those of the following formula:

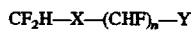

$$CF_2H-X-(CHF)_n-Y$$

wherein n is 0, 1 or 2, and X is CHF, $CF_2$ or $CH_2$, and Y is $CF_3$ or $CH_3$.

A further preferred group consists essentially of the following fluorinated hydrocarbons which may be used alone or in combination as the cleaning agent in the method of the invention:

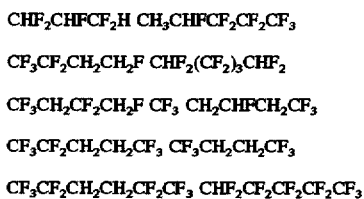

$CHF_2CHFCF_2H$    $CH_3CHFCF_2CF_2CF_3$ $CF_3CF_2CH_2CH_2F$    $CHF_2(CF_2)_3CHF_2$ $CF_3CH_2CF_2CH_2F$    $CF_3$    $CH_2CHFCH_2CF_3$ $CF_3CF_2CH_2CH_2CF_3$    $CF_3CH_2CH_2CF_3$ $CF_3CF_2CH_2CH_2CF_2CF_3$    $CHF_2CF_2CF_2CF_2CF_3$

The solvents and degreasers of the invention may be prepared by following the synthesis disclosed in F. A. Bloshchitso, A. I. Burmakov, b.v. Kunshenko, L. A. Alekkseeva and L. M. Yugopolski "Reaction of hydroxy and carbonyl compounds with sulfur tetrafluoride. XIV. Reaction of aliphatic oxocarboxylic acid with $SF_4$," Zh. Org. Khim., Volume 21, No. 7, 1985, pages 1414–1420 (English translation can be found in the Russian Journal of Organic Chemistry, Volume 21,. No. 7, 1985, pages 1286–1291). The hydrofluoroalkanes of the invention can also be prepared according to Zh. Org. Khim, 1980, 1401–1408 and 1982, 946 and 1168; Zh. Org. Khim. 1988, 1558; J. Chem. Soc. Perk. 1, 2258 (1980); J. Chem. Soc. Perk. Trans. 2, 1713 (1983); J. Chem. soc. C 1969, 1739; J. Chem. Soc. 1949, 2860; Zh. Anal. Khim. 1981 36 (6) 1125 (1181); J. Flourine chem. 1979, 325; Izv. Akad. Nauk SSSR, Ser. Khim. 1980, 2117 (in Russian); Rosz. Chem. 1974, (48), 1697 and J.A.C.S. 67, 1195 (1945); 72, 3577 (1950) and 76, 2343 (1954). Other methods for the preparation of the solvents and degreasers will readily occur to those skilled in the art.

The synthesis of the compounds described here is highly varied, depending on the structure of the molecule. However, general procedures will be applicable to the synthesis of many of these compounds. For example, the reduction of fluoroalkynes of the formula, $RC{\equiv}CR$ where R is H or F such as $CF_3CF_2C{\equiv}CCF_3$, provides access to compounds containing the —$CH_2CH_2$-grouping.

Perfluoroalkyl iodides, $R_fI$, are readily available commercially and are excellent raw materials for a variety of HFCs. For example, the $R_fI$ can be added to olefins at about 200° C. The addition to vinyl fluoride gives a mixture of a $R_fCHFCH_2I$ and $R_fCH_2CHFI$. Reduction of these adducts with e.g., Zn, gives a mixture of $R_fCH_2CH_2F$ and $R_fCH-FCH_3$ which can be separated by distillation. Thus, $CF_3CF_2CHFCH_3$, $CF_3CF_2CF_2CH_2CH_2F$ and similar compounds can be prepared.

Tosylation of commercially available fluorinated alcohols followed by reaction with KF gives compounds containing the —$CH_2F$ group. In this manner, $HCF_2CF_2CR_2CF_2CH_2F$ (from commercially available $HCF_2CF_2CF_2CF_2CH_2OH$), $CH_2F\ CF_2CF_2CF_2CH_2F$ (from $HOCH_2CF_2CF_2CH_2OH$), and $HCF_2CF_2CF_2CF_2CH_2F$ (from $HCF_2CF_2CF_2CF_2CH_2OH$) can be prepared. If the tosylate is first reacted with KI and then subsequently reduced with Zn, compounds such as $HCF_2CF_2CF_2CF_2CH_3$ can be prepared.

Compounds containing the $CH_2CHF$— moiety can be prepared either by the addition of HF to the corresponding olefin, or addition of HF to the corresponding alkyne (to give the —CH=CHF— group) followed by reduction. In this way, $CF_3CF_2CH_2CH_2F$ can be prepared from commercially available $CF_3CF_3CH_2{=}CH_2$, for example.

The addition of two fluorines to olefinic carbons can be effected by lead tetraacetate and HF. Thus, $CF_3CF_2CF_2CH{=}CH_2$ can be converted into $CF_3CF_2CF_2CHFCH_2F$.

Additional examples of various methods for preparing HFC's and fluorinated intermediates, in addition to those given above, can be found in specialized texts such as the laboratory manual and comprehensive compilation of M. Hudlicky, "Chemistry of Organic Fluorine Compounds", 2nd edition, Ellis Horwood Ltd., Chicester, UK, 1992.

Additives such as rust inhibitors, surfactants, corrosion inhibitors, decomposition inhibitors, acid scavengers, antioxidants, and emulsifiers in effective amounts (0.01 to 10 wt. %) may be added to the solvents to obtain additional desired properties. For example, alcohols can be added which enable the solvents to be used to remove solder fluxes from printed circuit boards. Inhibitors may be added to the solvent in effective amounts to inhibit decomposition react within undesirable decomposition products of the composition and/or prevent corrosion of metal surfaces. Any or all of the following classes of inhibitors may be employed in the invention: alkanols having 4 to 7 carbon atoms, nitroalkanes having 1 to 3 carbon atoms, 1,2-epoxyalkanes having 2 to 7 carbon atoms, phospshite esters having 12 to 30 carbon atoms, ethers having 3 to 4 carbon atoms, ketones having 3 to 5 carbon atoms, and amines having 5 to 8 carbon atoms. Other suitable inhibitors will readily occur to those skilled in the art. The inhibitors may be used alone or as mixtures in any proportion. Typically, up to about 2 percent of inhibitor based on the total weight of the mixture may be used.

The cleaning method of the invention removes most contaminants from the surface of a substrate by use of an effective amount of one or more solvents of the invention. By "effective amount" is meant the amount of solvent necessary to dissolve and remove the contaminant. for example, the present method removes organic contaminants such as mineral oils and synthetic oils from the surface of a substrate. Under the term "mineral oils," both petroleum-based and petroleum-derived oils are included. Lubricants such as engine oil, machine oil, and cutting oil are examples of petroleum-derived oils. The term "synthetic oils" embraces oils which do not contain petroleum-derived products, e.g., silicone oils.

The solvents of the invention also remove water from the surfaces of substrates. The method may be used in the single-stage or multistage drying of objects.

By extensive testing, it has been found that HFCs with at least 67% by weight fluorine generally do not have flashpoints. Similarly, it has been found that HFCs with more than 75% fluorine by weight are relatively poor solvents, especially for difficult-to-remove soils. Furthermore, the estimated solubility parameters, $\delta$, which are indicators of solvent power, generally are very low (less than 6.2) when the weight percent fluorine is high. Thus, the preferred compounds have 69–73 weight percent fluorine. This range of fluorine is low enough to provide good solvency and high enough to prevent flammability, and even allows small amounts of (flammable) beneficial additives to be incorporated without rendering the mixture flammable.

Although no solvent can clean all types of soils, the best solvents are those which have solvent properties which permit the cleaning of a variety of soils, including both polar soils, such as synthetic and semi-synthetic oils, and non-polar soils such as petroleum or mineral oils. The HFCs of this invention have a good balance of solvent properties, as judged by the polar and non-polar contributions to the total solubility parameter $\delta$. The degree of non-polar and polar contributions will vary, depending on the structure and percent fluorine. For example, the compound $CH_2FCHFCHFCF_2CF_3$ is relatively polar, and would be especially good for removing polar soils.

We have also found that the % fluorine generally affects the atmospheric lifetime. Although this depends on the distribution of hydrogens in the molecule, there is a trend indicating increased atmospheric lifetime with increasing fluorine content. Thus, butane, pentane, and hexane HFCs with only 1 or 2 hydrogens (>75% fluorine) have undesirably long lifetimes.

The HFCs of this invention have boiling points in the range of about 41° to 91° C. This range of boiling points provides a balance of two factors related to their use in solvent and cleaning applications. The first is that high boiling compounds require considerable energy consumption to maintain reflux, which is very commonly used in vapor cleaning and degreasing. However, if the boiling point is too low, substantial losses may result through evaporation and difficulty in condensing the vapors.

Thus, the HFCs of this invention provide an exceptional balance of the most desirable properties required for solvent cleaning, compared to the thousands of other HFCs that could be considered for solvent applications.

The method of the present invention may be used to clean the surface of inorganic and organic substrates. Examples of inorganic substrates include metallic substrates, ceramic substrates, and glass substrates. Examples of organic substrates include polymeric substrates such as polycarbonate, polystyrene, and acrylonitrile-butadiene-styrene (ABS). The method also cleans the surface of natural fabrics such as cotton, silk, fur, suede, leather, linen, and wool. The method also cleans the surface of synthetic fabrics such as polyester, rayon, acrylics, nylon, and blends thereof, and blends of synthetic and natural fabrics. It should also be understood that composites of the foregoing materials may be cleaned by the present method.

The method of the invention may be used in vapor degreasing, solvent cleaning, cold cleaning, dewatering, and dry cleaning. In these uses, the object to be cleaned is immersed in one or more stages in the liquid and/or vaporized solvent or is sprayed with the liquid solvent. Elevated temperatures, ultrasonic energy, and/or agitation may be used to intensify the cleaning effect.

In spraying applications, the solvents may be sprayed onto a surface by using a propellant (aerosol) or by some mechanical device. Suitable propellants include hydrochlorofluorocarbons like chlorodifluoromethane, hydrofluorocarbons such as 1,1,1,2-tetrafluoroethane, ethers like dimethyl ether and hydrocarbons like butane and isobutane.

The solvents of the invention are characterized as indicated above by a low or no flash point, and for the most part have a lifetime of less than ten years. Their solubility parameters range from 6.0 to 7.5 in $(Calories/cc)^{1/2}$.

The following Tables set forth preferred hydrofluoro carbons of the present invention including the predicted boiling point, the predicted lifetime in years, the calculated solubility parameters and the percent fluorine.

TABLE I

| Chemical Formula | Est. B.P. (°C.) | Est. Lifetime (Years) | Est. Solubility Parameters $(cal.cc)^2$ | % F |
|---|---|---|---|---|
| $CF_3CF_2(CHF)_2CH_3$ | 61.7 | ≦10 | 7.4 | 67.1 |
| $CF_3CF_2CHFCH_2F$ | 70 | ≦10 | 7.4 | 67.1 |
| $CHF_2CH_2CF_2CHF_2$ | 55.7 | ≦10 | 6.4 | 68.6 |
| $CF_3(CHF)_2CH_2F$ | 50.8 | ≦10 | 7.3 | 68.6 |
| $CF_3(CF_2)_3CH_2CH_3$ | 71 | ≦10 | 6.7 | 68.9 |
| $CF_3(CF_2)_2(CHF)_2CH_3$ | 86 | ≦10 | 7.5 | 68.9 |
| $CH_2FCH_2CF_2CF_2CF_3$ | 60.7 | ≦10 | 6.6 | 70.0 |
| $CF_2HCH_2CHFCF_2CF_3$ | 74.6 | ≦10 | 7.4 | 70.0 |
| $CH_2FCHFCHFCF_2CF_3$ | 75.5 | ≦10 | 7.4 | 70.0 |
| $CH_2FCF_2CH_2CF_2CF_3$ | 71.6 | 8–15 | 6.6 | 70.0 |
| $CF_3(CF_2)_3CHFCH_3$ | 75.4 | ≦10 | 6.8 | 71.4 |
| $CF_3(CF_2)_3CH_2CH_2F$ | 85.8 | ≦10 | 6.8 | 71.4 |
| $CH_2FCHFCF_2CF_3$ | 38 | ≦10 | 6.5 | 72.0 |
| $CF_2HCHFCHFCF_3$ | 51.9 | ≦10 | 7.5 | 72.0 |
| $CF_3(CF_2)_2CHFCH_2F$ | 62.3 | ≦10 | 7.4 | 73.0 |
| $CF_3CF_2CHFCH_2CF_3$ | 65.3 | 8–20 | 7.4 | 73.0 |
| $CF_3CHFCH_2CF_2CF_3$ | 66.5 | 8–20 | 7.4 | 73.0 |
| $CF_3(CHF)_2CF_3$ | 77.0 | 8–20 | 7.4 | 73.0 |
| $CF_3(CF_2)CH_2CHF_2$ | 63.6 | 8–15 | 6.5 | 73.0 |
| $CF_3CF_2CHFCF_2CH_2F$ | 68.1 | 8–15 | 7.4 | 73.0 |
| $CF_3CHF(CF_2)_2CF_3$ | 70.3 | 8–15 | 7.4 | 73.0 |
| $CHF_2(CF_2)_2CH_2F$ | 69.8 | 8–15 | 6.5 | 73.0 |
| $CHF_2CHF(CF_2)_3CF_3$ | 87.1 | ≦10 | 6.4 | 74.0 |
| $CHF_2CH_2(CF_2)_3CF_3$ | 88.7 | 8–20 | 6.4 | 74.0 |
| $CF_3CH_2CHF(CF_2)_2CF_3$ | 89.5 | 8–15 | 7.3 | 74.0 |
| $CF_3(CF_2)_2CH_2CHFCF_3$ | 84.9 | 8–15 | 7.3 | 74.0 |
| $CF_3CF_2CHFCHF_2$ | 37.4 | 8–15 | 6.0 | 75.0 |
| $CH_2F(CF_2)_3CF_3$ | 50.8 | 8–20 | 6.8 | 75.0 |
| $CF_2HCHF(CF_2)_2CF_3$ | 61.7 | 8–20 | 6.0 | 75.0 |
| $CF_3CF_2CHFCHFCF_3$ | 63.3 | 8–20 | 6.8 | 75.0 |
| $CF_3(CF_2)_4CH_2F$ | 75.9 | 8–20 | 6.6 | 76.0 |
| $CF_3(CF_2)_3CHFCHF_2$ | 86.8 | 8–20 | 7.4 | 76.0 |
| $CF_3CHFCF_2CHFCH_3$ | 68.0 | ≦10 | 7.4 | 67.1 |
| $CF_3CHFCHFCF_2CH_3$ | 72.9 | 8–20 | 7.4 | 67.1 |
| $CF_3CF_2CH_2CHFCH_2F$ | 75.2 | ≦10 | 7.4 | 67.1 |
| $CF_3CHFCF_2CH_2CH_2F$ | 76.8 | ≦10 | 7.4 | 67.1 |
| $CF_3CHFCH_2CF_2CH_2F$ | 83.1 | ≦10 | 7.4 | 67.1 |
| $CF_3CH_2CF_2CHFCH_2F$ | 84.2 | 8–15 | 7.4 | 67.1 |
| $CF_3CH_2CHFCF_2CH_2CH_2F$ | 85.4 | ≦10 | 7.4 | 67.1 |
| $CF_3(CHF)_3CH_2F$ | 89.1 | ≦10 | 7.4 | 67.1 |
| $CF_3CH_2CH_2CF_2CHF_2$ | 80.4 | ≦10 | 6.6 | 67.1 |

TABLE I-continued

| Chemical Formula | Est. B.P. (°C.) | Est. Lifetime (Years) | Est. Solubility Parameters $(cal.cc)^2$ | % F |
|---|---|---|---|---|
| $CF_3(CHF)_2CH_2CHF_2$ | 86.5 | ≦10 | 7.4 | 67.1 |
| $CF_3CHFCH_2CHFCHF_2$ | 87.7 | ≦10 | 7.4 | 67.1 |
| $CF_3CH_2(CHF)_2CHF_2$ | 90.4 | ≦10 | 7.4 | 67.1 |
| $CH_2FCH_2(CF_2)_2CHF_2$ | 79.7 | ≦10 | 6.6 | 67.1 |
| $CH_2F(CF_2)_2CH_2CHF_2$ | 87.1 | ≦10 | 6.6 | 67.1 |
| $CH_2FCF_2CH_2CF_2CHF_2$ | 87.2 | 8–15 | 6.6 | 67.1 |
| $CHF_2(CF_2)_2CHFCH_3$ | 69.2 | ≦10 | 7.4 | 67.1 |
| $CH_2FCHFCF_2CF_2CH_2F$ | 85.8 | ≦10 | 7.4 | 67.1 |
| $CH_2FCF_2CHFCF_2CH_2F$ | 88.1 | ≦10 | 7.4 | 67.1 |
| $CF_3CF_2(CH_2)_2CHF_2$ | 72.5 | ≦10 | 6.6 | 67.1 |
| $CF_3(CH_2)_2CHFCF_3$ | 72.9 | ≦10 | 7.4 | 67.1 |
| $CH_2F(CF_2)_3CH_3$ | 65.4 | 8–15 | 6.6 | 67.1 |
| $CHF_2CF_2CHFCH_2F$ | 55.3 | ≦10 | 7.3 | 68.6 |
| $CF_3CHFCH_2CHF_2$ | 50.8 | ≦10 | 7.3 | 68.6 |
| $CF_3CH_2CHFCHF_2$ | 53.0 | ≦10 | 7.3 | 68.6 |
| $CH_2F(CF_2)_2CH_3$ | 49.2 | ≦10 | 6.3 | 68.6 |
| $CHF_2(CF_2)_2CH_3$ | 35.8 | 10–30 | 6.5 | 68.6 |
| $CH_2FCHHFCF_2CHFCF_3$ | 80.1 | 8–15 | 7.4 | 70.1 |
| $CF_2HCFHCH_2CF_2CF_3$ | 77.9 | ≦10 | 7.4 | 70.1 |
| $CF_3CHFCH_2CHFCF_3$ | 76.2 | 8–30 | 6.6 | 70.1 |
| $CH_2FCHF(CF_2)_2CF_2H$ | 81.3 | ≦10 | 7.4 | 70.1 |
| $CF_3(CF_2)_2(CH_2)_2CF_3$ | 88.3 | 8–15 | 6.8 | 71.4 |
| $CF_3CF_2(CH_2)_2CF_2CF_3$ | 89.0 | 8–15 | 6.8 | 71.4 |
| $CHF_2(CF_2)_2CHFCHF_2$ | 80.7 | 8–15 | 7.4 | 73.0 |
| $CF_3CHFCF_2CF_2CF_3$ | 46.8 | 8–15 | 7.4 | 77.4 |

The following Table II sets forth a particularly preferred group of fluorinated hydrocarbons for use in the invention:

TABLE II

| Chemical Formula | Est. B.P. °C. | Est. Lifetime (Years) | Est. Solubility Parameters | % F |
|---|---|---|---|---|
| $CH_3CF_2CF_2CF_2H$ | 68 | 10–20 | 6.6 | 70.0 |
| $CHF_2CHFCHF_2$ | 41 | 5 | 6.4 | 70.9 |
| $CHF_2(CF_2)_2CHF_2$ | 43.0 | 16(M) | 6.0 | 75.0 |
| $CF_3CH_2CHFCH_2CF_3$ | 85 | 6–15 | 7.4 | 67.1 |
| $CF_3CH_2CH_2CF_3$ | 25 | 8–15 | 6.3 | 68.6 |
| $CF_3CF_2CH_2CH_2CF_3$ | 44.5–45 | 11 | 6.1 | 70.4 |
| $CHF_2CHFCHFCHF_2$ | 62–68 | 2–4 | 6.4 | 68.7 |
| $CF_3CF_2CH_2CH_2F$ | 44–46 | 2–4 | 6.5 | 68.7 |
| $CHF_2CHFCF_2CH_2F$ | 58–70 | 5–8 | 7.3 | 68.7 |

A further preferred group of fluorinated hydrocarbons are those of the formula:

$CF_3CH_2CF_2CH_2F$ $CHF_2CHFCF_2CF_2CF_2H$ $(CF_3CF_2CHF_2)$ $CFH_2CF_2CF_2CH_2F$

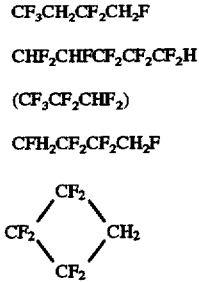

EXAMPLE I 1,1,2,2,3,3,4,4,5-Nonafluoropentane $HCF_2CF_2CF_2CF_2CH_2F)$

The alcohol $(H(CF_2)_4CH_2OH$, 104 g), 88 g tosyl chloride and 150 mL water were stirred mechanically and heated to 50° C. A solution of 20 g NaOH in 80 mL water was added over 0.5 h, keeping the temperature below 65° C. Stirring and heating were continued until the pH was neutral. The mixture was cooled and extracted with $CH_2Cl_2$. The organic layer was washed with 50 mL aq. ammonia, water, and dried over MgSO. Distillation gave 115 g colorless liquid, bp 110°–115° C. at 0.075 mm Hg (66% yield).

The above tosylate (301.5 g), 600 mL NMP, and 100 g KF were heated at 195° C. for 6 h to give 114.2 g of desired product; 6 C purity, 96%. Re-distillation provided 90% pure material, bp 82°–83.5° C. $^1$H NMR: 5.97 (tt, 1H) and 4.67 (dt, 2H) ppm. %F=73.

EXAMPLE II 1,1,1,4,4,4-Hexafluoro-2-(trifluoromethyl)butane

A 300 mL autoclave was charged with 21.0 g (0.1 mol) 4,4,4-trifluoro-3-(trifluoromethyl)butyric acid (prepared by hydrogenation and hydrolysis of commercially available ethyl 4,4,4-trifluoro-3-(trifluoromethyl)crotonate), 25 mL cyclohexane, and 38 g (0.35 mol) $SF_4$. The contents were heated to 65°–70° C. for 3 days, vented through a KOH scrubber, and poured into a separatory funnel containing 40 mL water. The aqueous layer was extracted with 2×25 mL portions of cyclohexane, and the combined organic layers distilled. An azeotrope of the desired product and cyclohexane was obtained (bp 41°–2° C.), which contained about 20% cyclohexane. The desired HFC was obtained in 23% yield following extraction with light mineral oil and distillation. A second distillation provided material of 99% purity, bp 43°–44° C. 1H NMR (CDC13): δ 3.25 (m, 1 H) and 2.63 (dq, 2 H); 19 F NMR: 67.3 (3 F) and 69.5 (5F) ppm. %F=70.

EXAMPLE III 1,1,2,2,3,3,4,4-Octafluoropentane

The tosylate of 2,2,3,3,4,4,5,5-octafluoropentanol was prepared according to Example I. The tosylate (117.2 g), 200 mL diethylene glycol (dried over 4 A sieves) and 70 g NaI were heated for 4 h to 150°–165° C. under a partial vacuum (100–120 mm Hg). The cold trap contained 73 g (93% pure) iodide, and after washing with water, weighed 70.3 g. It distilled at 64°–65° C. at 54 mm Hg.

The iodine (72.4 g) prepared as described above, was added to 63 mL tributyltin hydride over 2 h with stirring at <40° C., and the product was then distilled directly from the reaction mixture (38 g, 97% pure). Another distillation increased the purity to 99.5% (bp 67°–8° C.). 1H NMR: δ 1.83 (t, 3 H, J=18 Hz), 6.05 (tt, 1H, J-5 and 52 Hz). %F=73.

EXAMPLE IV 1,1,1,2,2,5,5,6,6,6-Decafluorohexane- ($CF_3CF_2CH_2CH_2CF_2CF_3$)

The reactor in this Example consisted of a 1.25 inch diameter Pyrex tube heated by means of electrical heating tape, and an internal thermocouple to measure the temperature inside the tube. The reactor was packed with a mixture of 50 cc 0.5% $Pd/Al_2O_3$ (⅛ inch pellets) and 100 cc glass helices for a total bed volume of 150 cc. Effluent from the reactor was condensed into cold traps maintained at −30° C. and −78° C. Hydrogen was passed into the tube at 155 mL/min, while $CF_3CF_2CCl_2CCl_2CF_2CF_3$ was metered into the top of the vertically mounted reactor at a rate of about 10 g/h. The temperature inside the reactor during the reduction was 202°–206° C. After a total reaction time of 3.75 h (38.1 g of the CFC added), 20.15 g of product was collected in the cold traps, which was 99% pure by GC. It was identified as $CF_3CF_2CH_2CH_2CF_2CF_3$, bp 66° C. (80% yield). 1H NMR (CDC13): δ 2.45 (t); 19F NMR: −87 and −122.5 ppm in a 3:2 ratio; MS: 247 (P-F) and base peak at m/e 177 (P-HF and $CF_3$), bp 66° C., %F=71.4.

EXAMPLE V 1,1,1,3,5,5,5-Heptafluoropentane 1,1,1,3,3,5,5,5-Octafluoropentane (total 16.6 g, 0.0768 mol) was introduced at a rate of 0.16 g per minute into the top of a vertically mounted Monel tube reactor (1 inch diameter) heated electrically to 365° C. The reactor was packed with 75 cc of 12–20 mesh Darco activated carbon. Nitrogen (50 cc/min) was passed through the reactor along with the organic material. Gases exiting the reactor were passed through an aqueous KOH scrubber followed by a cold trap at −78° C. A total of 11.45 g was collected in the cold trap. Analysis of this material by gas chromatography indicated 7.5% unreacted starting material, 41.3% trans-1, 1,1,3,5,5,5-heptafluoropent-2-ene and 47.2 of cis-1,1,1,3,5,5,5-heptafluoropent-2-ene, corresponding to a combined yield of the olefins of 71% and a $CF_3CH_2CF_2CH_2CF_3$ conversion of 95%. GC-MS of the olefin isomers were identical and had fragments at m/e 196 (parent), 177 (P-F), and 113 (P-$CH_2CF_3$).

The crude mixture of the above olefins was 60.3 g, of 79% purity (the remainder being primarily unreacted $CF_3CH_2CF_2CH_2CF_3$. The actual weight of the olefin isomers was therefore 47.6 g, 0.243 mol). This was stirred at room temperature with 0.39 g of 5% Rh on carbon under a hydrogen atmosphere of 20–40 psig. After 6 days, hydrogen uptake ceased and the catalyst was filtered. Fractional distillation through a 6-inch packed (0.16-inch Ni turnings) column gave 24.3 g (48.6%) of 1,1,1,3,5,5,5-heptafluoropentane, bp 85°–88° C. $^1$H NMR (CDC13): δ 5.12 apparent d of heptets (overlapping tt resulting from coupling to 2 sets of diastereotopic $CH_aH_b$ hydrogens), J=48 and 4 Hz, 1 H), 2.5 (m, 4 H); $^{19}$F NMR: −65.0 (6 F), −183.9 (1 F) ppm; $^{13}$C NMR; 125 (CF3, dq, $J_{CF}$=276 and 4 Hz), 82 (CHF, d of heptets, $J_{CF}$=176 and 3 Hz), 39.8 ($CH_2$, dq, $J_{CF}$=30 and 23 Hz) ppm, bp 85°–88° C., % F=67.

EXAMPLE VI

Performance studies are conducted wherein metal coupons are cleaned using the compounds of Table I as solvents. The metal coupons are soiled with various types of oils and dried so as to partially simulate conditions which occur while machining and grinding in the presence of these oils.

A test tube with condensing coils near its lips is used in this experiment. Each solvent is boiled in the test tube and condensed on the coils to provide adequate vapor. The condensed solvent is dripped back into the test tube.

The metal coupons are held in the solvent vapor and then vapor rinsed for a period of 15 seconds to 2 minutes depending upon the oils selected. Cleanliness (i.e. total residual materials left after cleaning) of the coupons is determined by measuring the weight change of the coupons using an analytical balance. The results indicate that the solvents of Table I are effective solvents, removing substantially all of the soil from the coupons.

EXAMPLE VII

Performance studies were conducted wherein metal coupons were cleaned using various HFC solvents. The metal coupons were soiled with various type of oils. These metal coupons were degreased in a small beaker with condenser coils around the lip to condense solvent and reduce losses and also to generate vapors to rinse the coupons.

Metal coupons are held in the solvent vapor and then vapor rinsed for a period of 15 seconds to 2 minutes depending upon the oils selected. Cleanliness testing of the coupons are done by measurement of the weight change of the coupons using an analytical balance to determine the total residual materials left after cleaning.

| Solvents Soil | Methyl Chloroform | CFC-113 | $CF_3CH_2CF_2CH_2CF_3$ | $CF_3CF_2CH_2CH_2CF_2CF_3$ | $CHF_2CHFCHF_2$ |
| --- | --- | --- | --- | --- | --- |
| Petroleum Oil | 98 | 93 | 57 | 55 | 25 |
| Synthetic Oil | 95 | 32 | 73 | 28 | 75 |

EXAMPLE VIII

The compatibility of various plastics in the solvents of Table I is measured by immersing the plastic in the solvent for a period of 2 to 10 minutes which stimulates at typical cleaning time for these materials in solvents. The visual observations are reported in Table II below. For purposes of this experiment "No Change" meant that visually no change in the color, size, texture and weight of the plastic was observed.

TABLE II

| MATERIAL | OBSERVATION |
| --- | --- |
| ABS | No Change |
| Acrylic | No Change |
| PVC | No Change |
| Nylon 66 | No Change |
| HDPE | No Change |
| Polypropylene | No Change |
| HIPS** | No Change |
| Polycarbonate | No Change |

*High density polyethylene
**High impact polystryene

The invention has been described with reference to certain preferred embodiments. However, as obvious variations thereon will become apparent to those skilled in the art, the invention is not to be considered as limited thereto.

What is claimed is:

1. A hydrofluoroalkane selected from those of the following formula:

$$CHF_2-X-(CHF)_n-X-Y$$

wherein X is selected from the group consisting of CHF, $CF_2$ and $CH_2$, Y is $CH_3$, and n is 0, 1 or 2.

* * * * *

UNITED STATES PATENT AND TRADEMARK OFFICE
CERTIFICATE OF CORRECTION

PATENT NO : 5,696,307
DATED : December 9, 1997
INVENTOR(S) : Van Der Puy et al.

It is certified that error appears in the above-identified patent and that said Letters Patent is hereby corrected as shown below:

Column 6, line 14, insert -- $CHF_2CF_2CHFCF_2CH_3$, 74.8, 8-20, 7.4, 67.1 --.

Column 6, line 51, delete "$CHF_2CHFCF_2CF_2CF_2H$" and substitute -- $CHF_2CHFCF_2CF_2H$ -- therefor.

Column 9, line 9, before Table, insert -- The results are shown in the attached table. --

Signed and Sealed this

Eleventh Day of January, 2000

Attest:

Q. TODD DICKINSON

*Attesting Officer*  *Acting Commissioner of Patents and Trademarks*